US007972612B2

(12) United States Patent
Hatano et al.

(10) Patent No.: US 7,972,612 B2
(45) Date of Patent: Jul. 5, 2011

(54) REMEDY FOR GLAUCOMA COMPRISING RHO KINASE INHIBITOR AND β-BLOCKER

(75) Inventors: Masakazu Hatano, Ikoma (JP); Tadashi Nakajima, Ikoma (JP); Takeshi Matsugi, Ikoma (JP); Hideaki Hara, Ikoma (JP)

(73) Assignee: Santen Pharmaceutical Co., Ltd., Osaka-Shi, Osaka (JP)

( * ) Notice: Subject to any disclaimer, the term of this patent is extended or adjusted under 35 U.S.C. 154(b) by 1026 days.

(21) Appl. No.: 10/535,000

(22) PCT Filed: Nov. 17, 2003

(86) PCT No.: PCT/JP03/14559
§ 371 (c)(1),
(2), (4) Date: May 16, 2005

(87) PCT Pub. No.: WO2004/045644
PCT Pub. Date: Jun. 3, 2004

(65) Prior Publication Data
US 2006/0052367 A1      Mar. 9, 2006

(30) Foreign Application Priority Data

Nov. 18, 2002 (JP) ............................... 2002-333213

(51) Int. Cl.
*A61K 9/00* (2006.01)
*A61K 31/535* (2006.01)
*A61K 31/44* (2006.01)

(52) U.S. Cl. ..................... 424/400; 514/236.2; 514/300; 514/913

(58) Field of Classification Search .................. None
See application file for complete search history.

(56) References Cited

U.S. PATENT DOCUMENTS

| 4,952,581 | A | | 8/1990 | Bito et al. |
| 5,502,052 | A | * | 3/1996 | DeSantis ..................... 514/236.2 |
| 6,187,304 | B1 | * | 2/2001 | Jin et al. ..................... 424/85.5 |
| 6,271,224 | B1 | | 8/2001 | Kapin et al. |
| 6,673,812 | B1 | * | 1/2004 | Azuma et al. .................. 514/303 |
| 2005/0014783 | A1 | * | 1/2005 | Dole et al. ..................... 514/310 |
| 2005/0043412 | A1 | | 2/2005 | Ichikawa et al. |
| 2005/0245509 | A1 | | 11/2005 | Nakajima et al. |

FOREIGN PATENT DOCUMENTS

| EP | 286903 A1 | 10/1988 |
| EP | 308135 A2 | 3/1989 |
| EP | 639563 A2 | 2/1995 |
| EP | 0 757 038 A1 | 2/1997 |
| EP | 0 253 717 A1 | 1/1998 |
| EP | 956865 A1 | 11/1999 |
| EP | 1034793 A1 | 9/2000 |
| JP | 7-508030 A | 9/1995 |
| JP | 2726672 B2 | 12/1997 |
| JP | 2001-509780 A | 7/2001 |
| JP | 63-79828 A | 5/2002 |
| JP | 2003-292442 A | 10/2003 |
| JP | 2004-513148 A | 4/2004 |
| WO | WO 90/02553 A1 | 3/1990 |
| WO | WO 93/16701 A2 | 9/1993 |
| WO | WO 93/23082 A1 | 11/1993 |
| WO | WO 94/06433 A1 | 3/1994 |
| WO | 95/28387 A1 | 10/1995 |
| WO | WO 97/23222 A1 | 7/1997 |
| WO | WO 98/06433 A1 | 2/1998 |
| WO | WO 00/09162 A1 | 2/2000 |
| WO | WO 00/25771 A1 | 5/2000 |
| WO | WO 00/57914 A1 | 10/2000 |
| WO | 02/38158 A1 | 5/2002 |
| WO | WO 02/38158 A1 | 5/2002 |
| WO | WO 03/049745 A1 | 6/2003 |

OTHER PUBLICATIONS

Konstas et al., The comparative ocular hypotensive effect of apraclonidine with timolol maleate in exfoliation versus primary open-angle glaucoma patients, Jun. 1999, Eye,13 (Pt3a), printed from http://www.ncbi.nlm.nih.gov/pubmed/10624424 on May 12, 2009, Abstract only, 2 pages.*

Abate M.A. et al., "Effect of Naproxen and Sulindac on Blood Pressure Response to Atenolol," *DICP—Annals. of Pharmacotherapy*, vol. 24, No. 9, 1990, pp. 810-813.

Zhou Yan et al., "Nonsteroidal Anti-Inflammatory Drugs Can Lower Amyloidogenic Aβ$_{42}$ by Inhibiting Rho," *Science*, vol. 302, No. 5648, Nov. 14, 2003, pp. 1215-1217.

Honjo et al., "Effects of Protein Kinase Inhibitor, HA1077, on Intraocylar Pressure and Outflow Facility in Rabbit Eyes," *Archived of Ophthalmology*, vol. 119, No. 8, Aug. 2001, pp. 1171-1178.

Database WPI Week 200060, Derwent Publications ltd., London, GB; AN 2000-628321 of WO 00/57914 (Santen Pharmaceutical Co., Ltd.; Oct. 5, 2002).

Clark A.F. et al., "Advances in Glaucoma Therapeutics," *Expert Opinion of Emerging Drugs*, 2002, United Kingdom, vol. 7, No. 1, May 2002, pp. 141-163.

(Continued)

*Primary Examiner* — Sreeni Padmanabhan
*Assistant Examiner* — Gigi Huang
(74) *Attorney, Agent, or Firm* — Holtz, Holtz, Goodman & Chick, P.C.

(57) ABSTRACT

A subject of the present invention is to find utility of a combination of a Rho kinase inhibitor having a novel action and a β-blocker as a therapeutic agent for glaucoma. Actions of reducing intraocular pressure are complemented and/or enhanced each other by combining the Rho kinase inhibitor with the β-blocker. For the administration mode, each drug can be administered in combination or in mixture.

2 Claims, 1 Drawing Sheet

OTHER PUBLICATIONS

Uehara, M. et al., "Calcium Sensitization of Smooth Muscle Mediated by a Rho-Associated Protein Kinase in Hypertension," *Nature*, (1997), 389, pp. 990 to 994.

Mariko Asahi et al., "Ryokunaisho to Ryokunaisho Chiryo Yakuzai (Fukuyaki Shido Manual II, Dai 10 Kai)," *The Pharmaceuticals Monthly*, (1996), 38(9), pp. 2311 to 2331.

Kuniteru Shirato, "I. Ryokunaisho no Yakubutsu Ryoho 1. Gairon" (Chiryoyaku no Sentaku o Dou Kangaerunoka), ("Some Practical Aspect in Medical Therapy") Ganka, (2002), 44(11), pp. 1443 to 1448.

Tatsuro Fukuchi, "I. Ryokunaisho no Yakubutsu Ryoho 2. Ryokunaisho Chiryoyaku C. Kokan Shinkei Sogaiyaku β Shadanyaku," ("β-Adrenergic Antagonists") Ganka, (2002), 44(11), pp. 1458 to 1463.

Ikuo Azuma et al., "Effects of Bunazosin Hydrochloride Ophthalmic Solution in Combination with Timolol Maleate Ophthalmic Solution in Patients with Open-Angle Glaucoma and Ocular Hypertension-Comparison with Dipivefrin Hydrochloride Ophthalmic Solution," *The Journal of the Eye*, (2002), 19(2), pp. 261 to 266.

Yuichiro Otake et al., "Effect and Safety of Combined Therapy with Betaxolol and isopropyl Unoprostone," *The Journal of the Eye*, (2000), 17(5), pp. 687 to 690.

Hideki Tokushige, "ROCK Sogaiyaku to Ryokunaisho" ("ROCK Inhibitor and Glaucoma"), *Bio Clinica*, (2002), 17(13), pp. 1191 to 1194.

Hoyng, P.F.J. et al., "Pharmacological Therapy for Glaucoma," *Drugs*, (2000), 59(3), pp. 411 to 434.

Megumi Honjo et al., "Effects of Rho-Associated Protein Kinase Inhibitor Y-27632 on Intraocular Pressure and Outflow Facility," *Invest. Ophthalmol. & Vis. Sci.*, vol. 42, No. 1 (2001). pp. 137-144.

P. Vasantha Rao et al., "Modulation of Aqueous Humor Outflow Facility by the Rho Kinase-Specific Inhibitor Y-27632," *Invest. Ophthalmol. & Vis. Sci.*, vol. 42, No. 5. (2001), pp. 1029-1037.

"Gekkan Ganka Shinryo Practice (Practical Ophthalmology)," 42, Tenganyaku no Tsukaikata (How to Use Eye Drops), 1999, pp. 52-53.

"Gekkan Yakuji (The Pharmaceuticals Monthly)," 1996, vol. 38, No. 9, pp. 2311-2331.

Hiromitsu Nagumo et al., "Rho Kinase Inhibitor HA-1077 Prevents Rho-Mediated Myosin Phosphatase Inhibition in Smooth Muscle Cells," *Am. J. Physiol.*, 278, C57-C65, (2000).

Demand for Trial dated Dec. 3, 2009 in the Trial for Invalidation for Japanese Patent 4,314,433.

Notice of Grounds of Rejection dated Aug. 27, 2007 in the Trial for Invalidation for Japanese Patent 4,314,433.

Board Decision in the Trial for Invalidation for Japanese Patent 4,314,433 translation dated Nov. 22, 2010.

Kyle A. Parrow et al., "Is It Worthwhile to Add Dipivefrin HC1 0.1% to Topical $\beta_1$~, $\beta_2$~blocker Therapy?", *Ophthalmology*, 96(9), 1338-1342 (1989.

Mark B. Abelson et al., "Sustained Reduction of Intraocular Pressure in Humans With the Calcium Channel Blocker Verapamil," *American Journal of Ophthalmology*, 105(2), 155-159 (1988).

Kristine A. Erickson et al., "Verapamil Increases Outflow Facility in the Human Eye," *Exp. Eye Res.* 61(5), 565-567 (1995).

Jing-Ming Dong et al., "cAMP-induced Morphological Changes Are Counteracted by the Activated RhoA Small GT Pase and the Rho Kinase ROKα*," *J. Bio. Chem.*, 273, No. 35, 22554-2:2562 (1998).

Roser Busca et al "Inhibition of Rho Is Required for cAMP-induced Melanoma Cell Differentiation," *Mol. Biol. Cell.*, 9(6), 1367-1378 (1998).

Michael Diestelhorst, "Combined therapy of Pilocarpine or Latanoprost with Timolol Versus Latanoprost Monotherapy," *Surv. Ophthalmology*, 47, Suppl 1. S155-S161 (2002).

Philip P. Ellis et al., "Aqueous Humor Pilocarpine and Timolol Levels After Instillation of the Single Drug or in Combination," *Invest. Ophthalmology & Visual Science*, 32(3), 520-522 (1991).

Asahi Kasei Press Release of Aug. 20, 2002.

Calbiochem General Catalog, 2002-2003.

WAKO Bio Window, 38 Mar. 2002.

"Ryokunaisho to Ganatsu (Glaucoma and Intraocular Pressure)," *Ganka* (Ophthalmology), No. 37.

* cited by examiner

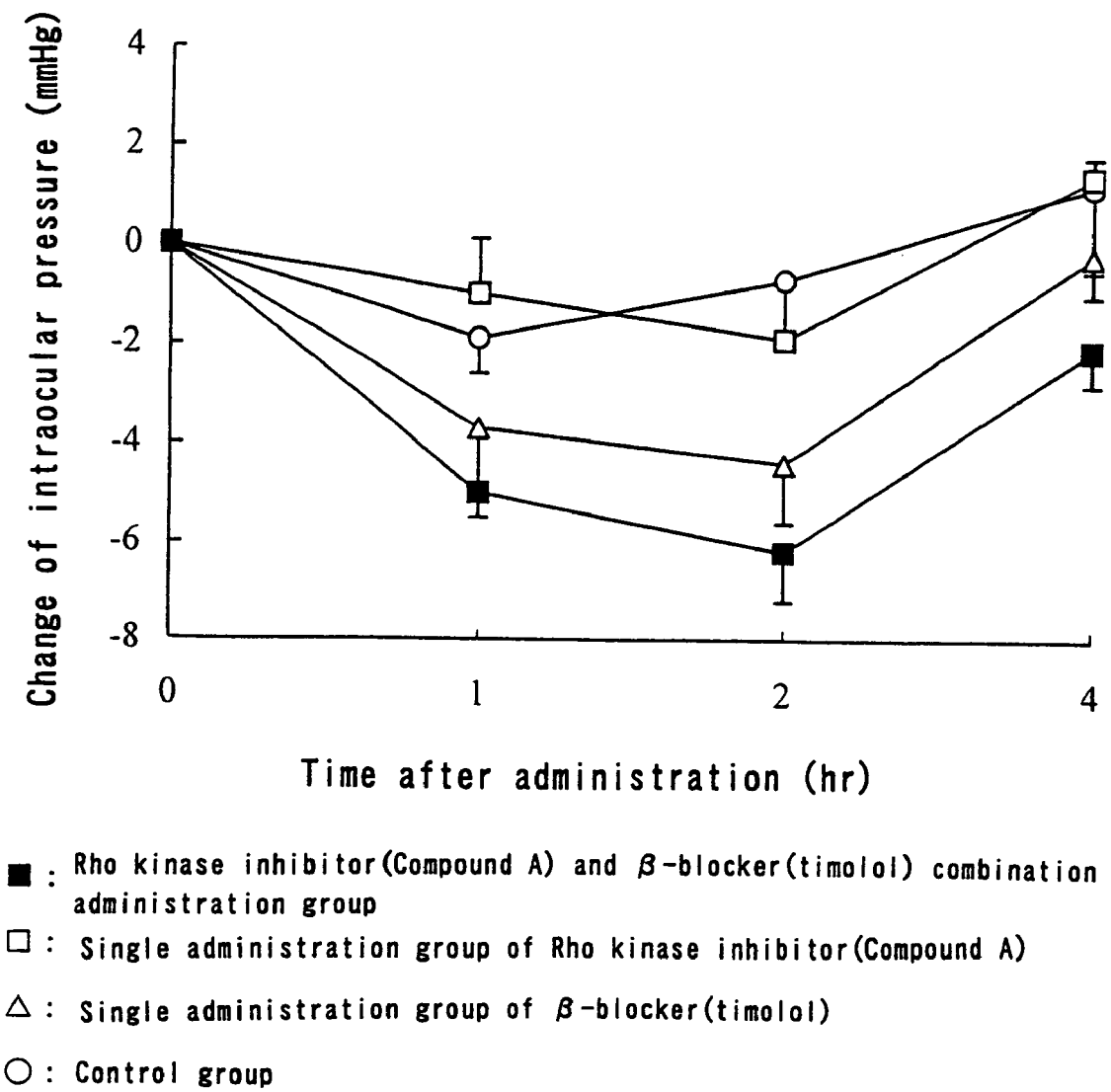

ic agent for glaucoma due to a combination of a Rho kinase inhibitor and a β-blocker.

REMEDY FOR GLAUCOMA COMPRISING RHO KINASE INHIBITOR AND β-BLOCKER

This application is the United States national phase application of International Application PCT/JP03/14559 filed Nov. 17, 2003.

TECHNICAL FIELD

The present invention relates to a therapeutic agent for glaucoma comprising the combination of a Rho kinase inhibitor and a β-Blocker.

BACKGROUND ART

Glaucoma is an intractable ocular disease with a risk of blindness, involving the increase of intraocular pressure due to various factors and the disorder of internal tissues of eyeballs (retina, an optic nerve and the like). A general method of treating glaucoma is intraocular pressure reduction therapy, which is exemplified by pharmacotherapy, laser therapy, surgical therapy and the like.

For the pharmacotherapy, drugs such as sympathomimetic agents (nonselective stimulants such as epinephrine, $\alpha_2$ stimulants such as apraclonidine), sympatholytic agents (β-blockers such as timolol, befunolol, carteolol, nipradilol, betaxolol, levobunolol and metipranolol and $\alpha_1$-blockers such as bunazosin hydrochloride), parasympathomimetic agents (pilocarpine and the like), carbonic anhydrase inhibitors (acetazolamide and the like) and prostaglandins (isopropyl unoprostone, latanoprost, travoprost, bimatoprost and the like) have been used.

Recently, a Rho kinase inhibitor was found to serve as a therapeutic agent for glaucoma based on a new mechanism of action (WO 00/09162). Invest. Ophthalmol. & Vis. Sci., 42 (1), 137-144 (2001) discloses that the Rho kinase inhibitor increases the aqueous humor outflow from a trabecular meshwork outflow pathway thereby reducing intraocular pressure, and Invest. Ophthalmol. & Vis. Sci., 42 (1), 137-144 (2001) and Invest. Ophthalmol. & Vis. Sci., 42 (5), 1029-1037 (2001) suggest that the action is due to a change of cytoskeleton in trabecular meshwork cells.

Combined use of drugs having actions of reducing intraocular pressure to treat glaucoma has already been studied and there are some reports on the studies. For example, Japanese Patent No. 2726672 reports combined administration of the sympatholytic agent with prostaglandins. WO 02/38158 discloses a method of treating glaucoma by administering some drugs having actions of reducing intraocular pressure in combination to eyes.

However, any reports do not describe the Rho kinase inhibitor at all, and naturally, there is no description concerning advantageous effects brought about by combining the Rho kinase inhibitor with a β-blocker, either.

As mentioned above, neither study nor report has been made concerning therapeutic effects on glaucoma obtained by combining the Rho kinase inhibitor with the β-blocker, so far.

DISCLOSURE OF THE INVENTION

It is a very interesting subject to find utility as a therapeutic agent for glaucoma due to a combination of a Rho kinase inhibitor and a β-blocker.

Studying precisely effects due to the combination of a Rho kinase inhibitor and a β-blocker, the present inventors found that an action of reducing intraocular pressure is increased and/or persistence of the action is improved by combining these drugs compared with a case where each drug is used alone and consequently completed the present invention. Detailed test methods and their effects are described later under the item of "Pharmacological Tests". A remarkable increase in action of reducing intraocular pressure and/or remarkable improvement of persistence of the action was observed by combining a Rho kinase inhibitor with a β-blocker. The present invention can be suitably used for treating and preventing ophthalmopathy accompanied by a rise of intraocular pressure.

The increase in the action of reducing intraocular pressure and/or persistence of the action is improved by administering the combination of the Rho kinase inhibitor and the β-blocker to eyes. Accordingly, the present invention is useful as a therapeutic agent for glaucoma.

The present invention relates to a therapeutic agent for glaucoma comprising the combination of a Rho kinase inhibitor and a β-blocker. These drugs complement and/or enhance their actions each other.

For the method of administration, each of the Rho kinase inhibitor and the β-blocker can be in a separate preparation and these drugs can be administered in combination. Alternatively, these drugs can be formulated in a single preparation to be administered. In other words, these drugs can be administered in mixture.

The Rho kinase inhibitors and the β-blockers of the present invention include salts thereof. When these compounds have a basic group such as an amino group, they can be salts with an inorganic acid such as hydrochloric acid or nitric acid or with an organic acid with oxalic acid, succinic acid, acetic acid or maleic acid. When they have an acidic group such as a carboxyl group, they can be salts with an alkali metal such as sodium or potassium or with an alkaline earth metal such as calcium.

The Rho kinase inhibitors and the β-blockers of the present invention include derivatives thereof such as esters. Specific examples of esters are alkyl esters such as methyl esters, ethyl esters and isopropyl esters.

Further, the Rho kinase inhibitors and the β-blockers of the present invention can be in the form of hydrates or solvates.

The present invention is characterized by treating glaucoma with the combination of a Rho kinase inhibitor and a β-blocker.

The Rho kinase inhibitor in the present invention means a compound which inhibits serine/threonine kinase activated with activation of Rho. Examples of such compounds are the compounds which inhibit ROKα (ROCK-II), p160ROCK (ROKβ, ROCK-I) and other compounds which inhibit proteins having a serine/threonine kinase activity. Specific Rho kinase inhibitors are exemplified by Rho kinase inhibitors such as (R)-trans-N-(pyridin-4-yl)-4-(1-aminoethyl)cyclohexanecarboxamide and (R)-(+)-N-(1H-pyrrolo[2,3-b]pyridin-4-yl)-4-(1-aminoethyl)-benzamide disclosed in WO 98/06433 and WO 00/09162, Rho kinase inhibitors such as 1-(5-isoquinolinesulfonyl)homopiperazine and 1-(5-isoquinolinesulfonyl)-2-methylpiperazine disclosed in WO 97/23222 and Nature, 389, 990-994 (1997), Rho kinase inhibitors such as (1-benzylpyrrolidin-3-yl)-(1H-indazol-5-yl)amine disclosed in WO 01/56988, Rho kinase inhibitors such as (1-benzylpiperidin-4-yl)-(1H-indazol-5-yl)amine disclosed in WO 02/100833, Rho kinase inhibitors such as N-[2-(4-fluorophenyl)-6,7-dimethoxy-4-quinazolinyl]-N-(1H-indazol-5-yl)amine disclosed in WO 02/076976, Rho kinase inhibitors such as N-4-(1H-indazol-5-yl)-6,7-dimethoxy-N-2-pyridin-4-yl-quinazolin-2,4-diamine disclosed in WO 02/076977 and Rho kinase inhibitors such as 4-methyl-5-(2-methyl-[1,4]diazepan-1-sulfonyl)isoquinoline disclosed in WO 99/64011.

On the other hand, any β-blockers having the action of reducing intraocular pressure and utility in treating glaucoma can be used. β-Blockers having the action of reducing intraocular pressure are specifically exemplified by timolol, befunolol, carteolol, nipradilol, betaxolol, levobunolol and metipranolol, which have already been on the market as a therapeutic agent of glaucoma. These are preferably used.

Glaucoma in the present invention includes primary open angle glaucoma, normal intraocular tension glaucoma, hypersecretion glaucoma, ocular hypertension, acute angle-closure glaucoma, chronic closed angle glaucoma, combined-mechanism glaucoma, corticosteroid glaucoma, amyloid glaucoma, neovascular glaucoma, malignant glaucoma, capsular glaucoma, plateau iris syndrome and the like.

To carry out the present invention, preparations can be two preparations prepared by formulating a Rho kinase inhibitor and a β-blocker separately or one preparation prepared by mixing these ingredients. Particular techniques are unnecessary for the formulation, and the preparations can be prepared using widely-used techniques. A preferred method of administration is eye topical administration, and a preferred dosage form is an ophthalmic solution or an eye ointment.

When a Rho kinase inhibitor and a β-blocker are formulated in preparations separately, each preparation can be prepared according to known methods. For example, the Rho kinase inhibitor can be formulated in preparations by referring to Formulation Examples described in the above-mentioned International Publications (WO 00/09162 and WO 97/23222). As the preparations of the β-blocker, preparations of timolol, befunolol, carteolol, nipradilol, betaxolol, levobunolol, metipranolol and the like can be used. These preparations have already been on the market as the therapeutic agent of glaucoma.

The formulation containing a Rho kinase inhibitor and a β-blocker in mixture can be also prepared according to known methods. The ophthalmic solutions can be prepared, using isotonic agents such as sodium chloride and concentrated glycerin; buffers such as sodium phosphate buffer and sodium acetate buffer; surfactants such as polyoxyethylene sorbitan monooleate, stearate polyoxyl 40, and polyoxyethylene hardened castor oil; stabilizers such as sodium citrate and sodium edetate; and preservatives such as benzalkonium chloride and paraben, as needed.

The pH should be within an ophthalmologically acceptable range and is preferably within a range from pH 4 to pH 8. For reference, a formulation example thereof is described below in the section of Example. However, the formulation example never limits the scope of the invention.

The present invention also relates to a method of treating glaucoma comprising administering effective amounts of the Rho kinase inhibitor in combination with the β-blocker to a patient. By administering the effective amounts of the Rho kinase inhibitor in combination with the β-blocker to the patient, they complement and/or enhance their actions each other. Rho kinase inhibitors which are suitable for the method of treatment are (R)-trans-N-(pyridin-4-yl)-4-(1-aminoethyl)cyclohexanecarboxamide, (R)-(+)-N-(1H-pyrrolo[2,3-b]pyridin-4-yl)-4-(1-aminoethyl)benzamide, 1-(5-isoquinolinesulfonyl)homopiperazine and 1-(5-isoquinolinesulfonyl)-2-methylpiperazine. β-Blockers which are suitable for the method of treatment are timolol, befunolol, carteolol, nipradilol, betaxolol, levobunolol and metipranolol.

The doses of a Rho kinase inhibitor and a β-blocker can be determined depending on the symptom and age of patients, the dosage form, the administration route and the like. The case of instillation is briefly described below. The dose of the Rho kinase inhibitor varies depending on the drug type. The Rho kinase inhibitor can be administered generally within a range from 0.025 to 10,000 μg daily from once to several times a day. The dose can be appropriately raised or lowered depending on the age and symptom of patients and the like.

The dose of a β-blocker varies depending on drug type. The usual daily dose is within a range from 5 to 5,000 μg, which can be administered from once to several times a day. More specifically, timolol is generally administered at a daily dose of 5 to 1,500 μg, befunolol is administered at a daily dose of 10 to 2,000 μg, carteolol is administered at a daily dose of 10 to 5,000 μg, nipradilol is administered at a daily dose of 10 to 1,250 μg, betaxolol is administered at a daily dose of 50 to 1,000 μg, levobunolol is administered at a daily dose of 5 to 5,000 μg, and metipranolol is administered at a daily dose of 5 to 5,000 μg. Depending on the age, symptoms and the like of patients, the doses can be varied. Based on similar standards, the doses of the other β-blockers can be determined.

These doses are also applicable to the administration of the combination of a Rho kinase inhibitor and a β-blocker. In case that a Rho kinase inhibitor and a β-blocker are to be administrated in one formulation, the formulation should be prepared by selecting the mixing ratio of two drugs appropriately so that their daily doses might not excess each dose of the separate drugs. The mixed formulation can be administered from once to several times daily.

BRIEF DESCRIPTION OF DRAWINGS

FIG. 1 is a graph showing changes of intraocular pressure with time in respective administration groups.

BEST MODE FOR CARRYING OUT THE INVENTION

A formulation example and pharmacological tests are shown in the following Examples. The Examples are for better understanding of the invention but never limits the scope of the invention.

EXAMPLES

Formulation Example

A general formulation example of an ophthalmic solution comprising a Rho kinase inhibitor ((R)-(+)-N-(1H-pyrrolo[2,3-b]-pyridin-4-yl)-4-(1-aminoethyl)benzamide dihydrochloride) and a β-blocker (timolol) in the present invention is shown below.
Ophthalmic Solution (in 100 mL)
(R)-(+)-N-(1H-Pyrrolo[2,3-b]pyridin-4-yl)-4-(1-aminoethyl)benzamide

| dihydrochloride | 0.1 g |
| Timolol maleate | 0.34 g |
| Boric acid | 0.2 g |
| Concentrated glycerin | 0.25 g |
| Benzalkonium chloride | 0.005 g |
| Diluted hydrochloric acid | quantum sufficient |
| Sodium hydroxide | quantum sufficient |
| Purified water | quantum sufficient |

Ophthalmic solutions having desired combinations and desired concentrations can be prepared by changing the kinds and amounts of a Rho kinase inhibitor and a β-blocker and by appropriately changing the amounts of the additives.

Pharmacological Tests

So as to study the utility of the combination of a Rho kinase inhibitor and a β-blocker, they were administered to experimental animals, examining the effect on reducing intraocular pressure. (R)-(+)-N-(1H-Pyrrolo[2,3-b]pyridin-4-yl)-4-(1-aminoethyl)benzamide dihydrochloride [Compound A] was used as the Rho kinase inhibitor. Timolol was used as the β-blocker.

Preparation of Test Compound Solutions

1. Preparation of Rho Kinase Inhibitor Solutions

The Rho kinase inhibitor was dissolved in physiological saline, and then sodium hydroxide was added to the solution to neutralize it (pH 6.0 to 7.0) to thereby prepare Rho kinase inhibitor solutions having desired concentrations.

2. Preparation of β-blocker Solutions

A commercially available β-blocker ophthalmic solution was used as it was, or was diluted with physiological saline to prepare β-blocker solutions having desired concentrations.

Method of Test

Administering the combination of the Rho kinase inhibitor and the β-blocker, the effect on reducing intraocular pressure was studied. As a reference, administering the Rho kinase inhibitor alone or the β-blocker alone, the effect on reducing intraocular pressure was also studied. As a control, only a vehicle (physiological saline) was administered.

Drugs and Animals to be Used for Tests

Rho kinase inhibitor solution: 0.1% compound A solution (instillation dosage: 50 μl)

β-Blocker solution: Timolol ophthalmic solution (trade name: Timoptol 0.25%, instillation dosage: 50 μl)

Experimental animal: Japanese white rabbit (strain: JW, sex: male, four rabbits per group)

Method of Administration and Method of Measurement

1. Administration of the combination of a Rho kinase inhibitor and a β-blocker

1) One drop of a 0.4% oxybuprocaine hydrochloride ophthalmic solution (trade name: Benoxil solution 0.4%) was instilled into both eyes of each experimental animal to anesthetize it topically.

2) Intraocular pressure was measured immediately before administering the test compound solution, and the intraocular pressure was referred to as initial intraocular pressure.

3) The Rho kinase inhibitor solution was instilled into one eye of each experimental animal (the other eye was not treated). Since it is impossible to instill the β-blocker solution at the same time, after a short period (about five minutes), the β-blocker solution was instilled into the same eye.

4) One, two and four hours after instilling the Rho kinase inhibitor solution, one drop of the 0.4% oxybuprocaine hydrochloride ophthalmic solution was instilled into both eyes to anesthetize them topically. Then intraocular pressure was measured three times to obtain the average of three measurements.

2. Single Administration of a Rho Kinase Inhibitor

Each test was carried out in the same manner as in the above-mentioned combination administration test except that the β-blocker solution was replaced with physiological saline.

3. Single Administration of a β-Blocker

Each test was carried out in the same manner as in the above-mentioned combination administration test except that the Rho kinase inhibitor solution was replaced with physiological saline.

4. Control

Each test was carried out in the same manner as in the above-mentioned combination administration test except that the Rho kinase inhibitor solution and the β-blocker solution were replaced with physiological saline.

Results and Consideration

Results of the tests are shown in FIG. 1. Intraocular pressure is expressed in each change from initial intraocular pressure.

As apparent from FIG. 1, the Rho kinase inhibitor and β-blocker combination group exhibited an excellent action of reducing intraocular pressure compared with single administration groups of each drug, namely the single administration group of the Rho kinase inhibitor and the single administration group of the β-blocker, and exhibited improvement of persistence of the action.

When combinations of the other Rho kinase inhibitors and the other β-blockers disclosed in the specification were tested, tendencies similar to the above-mentioned test results were also observed.

The above-mentioned results show that a stronger reducing effect on intraocular pressure and/or improvement of persistence is obtained by combining the Rho kinase inhibitor with the β-blocker.

INDUSTRIAL APPLICABILITY

The present invention provides a therapeutic agent for glaucoma comprising the combination of a Rho kinase inhibitor and a β-blocker.

The invention claimed is:

1. A therapeutic agent for glaucoma comprising a combination of pharmaceutically effective amounts of (i) a Rho kinase inhibitor and (ii) a β-blocker, wherein the Rho kinase inhibitor is (R)-(+)-N-(1H-pyrrolo[2,3-b]pyridin-4-yl)-4-(1-aminoethyl)benzamide and the β-blocker is timolol.

2. A method of treating glaucoma comprising administering effective amounts of a Rho kinase inhibitor in combination with a β-blocker to a patient wherein the Rho kinase inhibitor is (R)-(+)-N-(1H-pyrrolo[2,3-b]pyridin-4-yl)-4-(1-aminoethyl)benzamide and the β-blocker is timolol.

* * * * *